(12) United States Patent
Shimamoto et al.

(10) Patent No.: US 8,097,654 B2
(45) Date of Patent: Jan. 17, 2012

(54) RADIOLABELED 3-[3-(BENZOYL-AMIDO)BENZYLOXY] ASPARTIC ACID DERIVATIVE AND METHOD OF PRODUCING THE SAME

(75) Inventors: Keiko Shimamoto, Suita (JP); Hideo Saji, Kyoto (JP); Yuji Kuge, Kyoto (JP); Masashi Ueda, Kyoto (JP); Masamichi Satoh, Kyoto (JP); Takayuki Nakagawa, Kyoto (JP)

(73) Assignee: Suntory Holdings Limited, Osaka-shi, Osaka (JP)

( * ) Notice: Subject to any disclaimer, the term of this patent is extended or adjusted under 35 U.S.C. 154(b) by 844 days.

(21) Appl. No.: 10/593,034

(22) PCT Filed: Mar. 18, 2005

(86) PCT No.: PCT/JP2005/005600
§ 371 (c)(1),
(2), (4) Date: Sep. 15, 2006

(87) PCT Pub. No.: WO2005/090268
PCT Pub. Date: Sep. 29, 2005

(65) Prior Publication Data
US 2008/0248485 A1    Oct. 9, 2008

(30) Foreign Application Priority Data

Mar. 18, 2004 (JP) .................................. 2004-79116

(51) Int. Cl.
*A61K 31/166* (2006.01)
*A61K 31/167* (2006.01)
*C07C 237/40* (2006.01)

(52) U.S. Cl. ........................................ 514/617; 564/161
(58) Field of Classification Search .................... None
See application file for complete search history.

(56) References Cited

U.S. PATENT DOCUMENTS

| 7,247,652 B2 * | 7/2007 | Shimamoto ................ 514/533 |
| 2002/0055524 A1 * | 5/2002 | Maynard et al. |
| 2002/0128236 A1 * | 9/2002 | Maynard et al. |
| 2002/0182169 A1 * | 12/2002 | Hunter et al. |
| 2003/0149250 A1 * | 8/2003 | Kung et al. |
| 2006/0051293 A1 * | 3/2006 | Kung et al. |

FOREIGN PATENT DOCUMENTS

| WO | WO 02/20480 A1 * | 3/2002 |
| WO | WO 02/20492 A1 * | 3/2002 |
| WO | WO 02/070020 A2 * | 9/2002 |
| WO | WO 02/085903 A2 * | 10/2002 |
| WO | 03/000698 | 1/2003 |
| WO | WO 03/000698 * | 1/2003 |
| WO | WO 03/018070 A1 * | 3/2003 |

OTHER PUBLICATIONS

Karina Aprico et al., "[³H](2S,4R)-4-Methylglutamate: A Novel Ligand for the Characterization of Glumate Transporters", Journal of Neurochemistry, 77, 2001, pp. 1218-1225.
Suzanne Killinger et al., "Autoradiographic Studies Indicate Regional Variations in the Characteristics of L-Glutamate Transporters in the Rat Brain", Neuroscience Leters 216, Aug. 1996, pp. 101-104.
Shimamoto et al., "Characterization of Novel L-threo-β-Benzyloxyaspartate Derivatives, Potent Blockers of the Glutamate Transporters," Molecular Pharmacology, vol. 65, No. 4, pp. 1008-1015 (2004).
Anderson et al., "Differing effects of substrate and non-substrate transport inhibitors on glutamate uptake reversal," Journal of Neurochemistry, vol. 79, pp. 1207-1216 (2001).
Shimamoto et al., "DL-threo-β-Benzyloxyaspartate, a Potent Blocker of Excitatory Amino Acid Transporters," Molecular Pharmacology, vol. 53, pp. 195-201 (1998).
Chatton et al., "Effects of glial glutamate transporter inhibitors on intracellular Na⁺ in mouse astrocytes," Brain Research vol. 893, pp. 46-52 (2001).
Lebrun et al., "New β-Hydroxyaspartate Derivatives are Competitive Blockers for the Bovine Glutamate/Aspartate Transporter," Journal of Biological Chemistry, vol. 272, No. 33, pp. 20336-20339 (1997).
Shigeri et al., "Effects of threo-β-hydroxyaspartate derivatives on excitatory amino acid transporters (EAAT4 and EAAT5)," Journal of Neurochemistry, Vol. 79, pp. 297-302 (2001).

* cited by examiner

Primary Examiner — Yong Chu
Assistant Examiner — Michael Barker
(74) Attorney, Agent, or Firm — Drinker Biddle & Reath LLP

(57) ABSTRACT

The present invention provides a radiolabeled ligand which is highly selective and potent for glutamate transporters and is usable in specifically detecting the glutamate transporter.
Specifically, the present invention provides a 3-[3-(benzoylamido)benzyloxy]aspartic acid having a radioactive substituent on the benzoyl group which is represented by the following formula (1), or an ester or salt thereof:

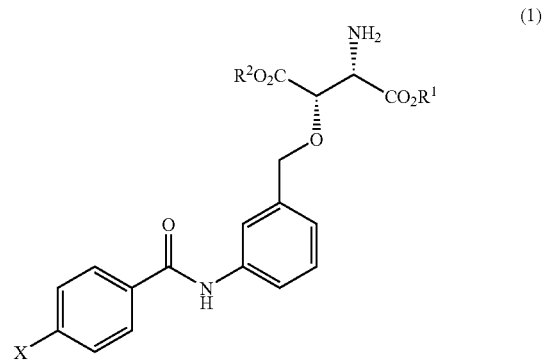

wherein X represents a substituent containing a radioactive atom(s) which is selected from a straight or branched lower aliphatic alkyl group, a hydroxyl group, a straight or branched lower aliphatic alkoxy group, an amino group, a straight or branched lower aliphatic acylamido group, a halogen atom and a straight or branched lower aliphatic haloalkyl group; and R¹ and R² each represents a hydrogen atom, a straight or branched lower aliphatic alkyl group or an acetoxymethyl group.

11 Claims, 7 Drawing Sheets

Radiochromatogram obtained by TLC

Compound : [$^1$H] Et-B$_z$A-TBOA
Solvent system
  and Radiochemical purity : 97.1%
  1-Butanol/Acetic acid/water (4/1/2, v/v/v)

TP-751

Front

Origin

Hot  Std  Mix

Group 1

| No | Index | Name | PSL | A (mm2) | PSL/A | PSL-BG | (PSL-BG)/A | Calibrated | %fGrp |
|---|---|---|---|---|---|---|---|---|---|
| 1 | A-1 |  | 561.14 | 1414.40 | 0.40 | 458.61 | 0.32 |  | 2.30 |
| 1 | A-2 |  | 19328.23 | 166.44 | 116.13 | 19316.16 | 116.05 |  | 97.07 |
| 1 | A-3 |  | 188.77 | 873.64 | 0.22 | 125.43 | 0.14 |  | 0.63 |
| 1 | A-4 BG |  | 10.91 | 150.48 | 0.07 | 0.00 | 0.00 |  | 0.00 |

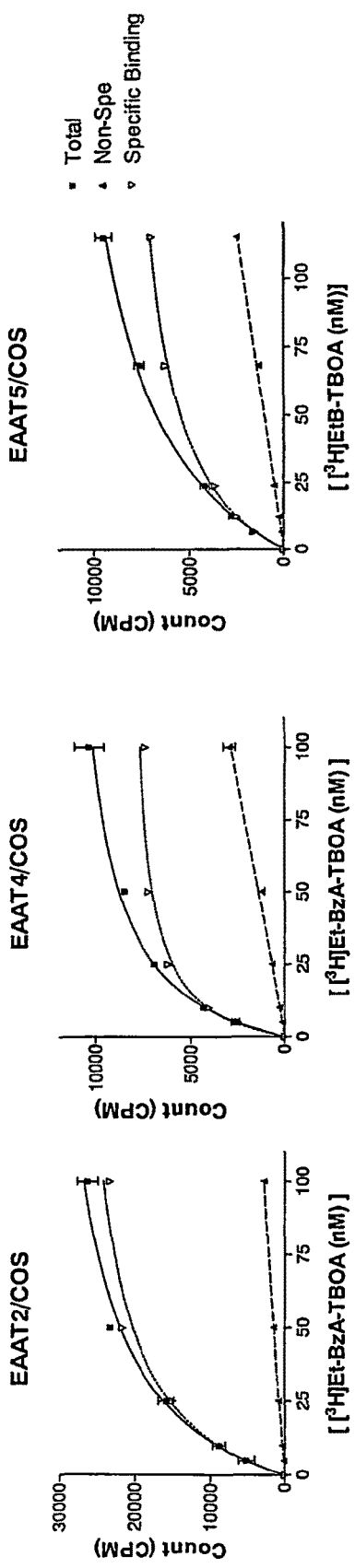
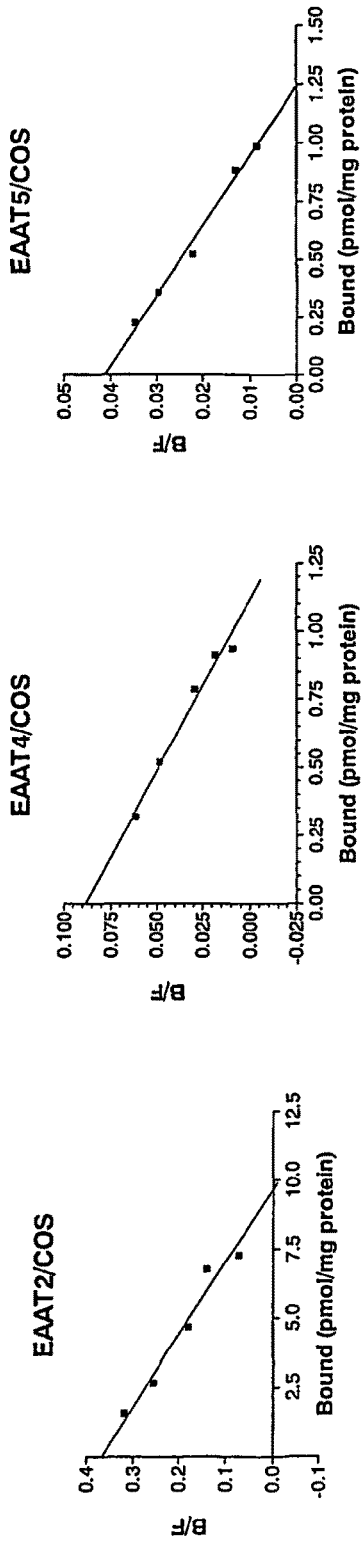
Fig. 7
Fig. 8

RADIOLABELED 3-[3-(BENZOYL-AMIDO)BENZYLOXY]ASPARTIC ACID DERIVATIVE AND METHOD OF PRODUCING THE SAME

CROSS REFERENCE TO RELATED APPLICATIONS

This application is a National Stage of International Application No. PCT/JP2005/005600, filed Mar. 18, 2005, and which claims benefit of Japanese Application No. 2004-079116 filed May 12, 2005.

TECHNICAL FIELD

This invention relates to radiolabeled L-glutamate uptake inhibitors. More specifically, the invention relates to a 3-[3-(benzoylamido)benzyloxy]aspartic acid derivative which is capable of inhibiting glutamate uptake by L-glutamate transporter and contains a radioactive atom(s), which is represented by the following formula (1), wherein X represents a substituent containing a radioactive atom(s) which is selected from a straight or branched lower aliphatic alkyl group, a hydroxyl group, a straight or branched lower aliphatic alkoxy group, an amino group, a straight or branched lower aliphatic acylamido group, a halogen atom and a straight or branched lower aliphatic haloalkyl group; and $R^1$ and $R^2$ each represents a hydrogen atom, a straight or branched lower aliphatic alkyl group or an acetoxymethyl group; a precursor compound of a compound of the formula (1) which is represented by the following formula (2), wherein, $R^1$ and $R^2$ each represents a hydrogen atom, a straight or branched lower aliphatic alkyl group or an acetoxymethyl group; Y represents a leaving group to undergo a substitution reaction which is selected from an organometallic group, a halogen atom, a diazo group, a diazonium group, a trialkylammonium group and a nitro group; and Boc represents a t-butoxycarbonyl group; a precursor compound of the compound of the formula (1) wherein X is a tritium-containing aliphatic alkyl group, and each of $R^1$ and $R^2$ is a hydrogen atom, which is represented by the formula (3) wherein $R^3$ represents a straight or branched lower unsaturated aliphatic alkenyl group, e.g., a vinyl group, a propenyl group, an allyl group or a butenyl group; a method of producing a compound of the formula (1) from a compound of the formula (2); a method of producing a compound of the formula (1) wherein X is a tritium-containing aliphatic alkyl group, and each of $R^1$ and $R^2$ is a hydrogen atom from a compound of the formula (3); and a method of examining a biological sample with the use of a compound of the formula (1).

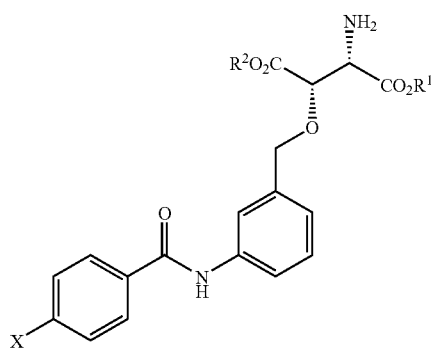

(1)

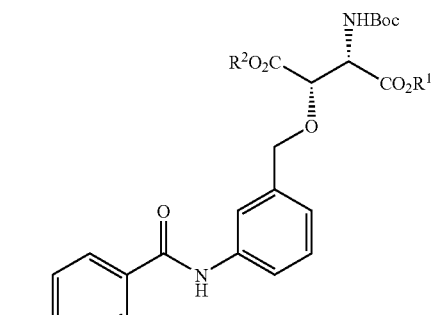

(2)

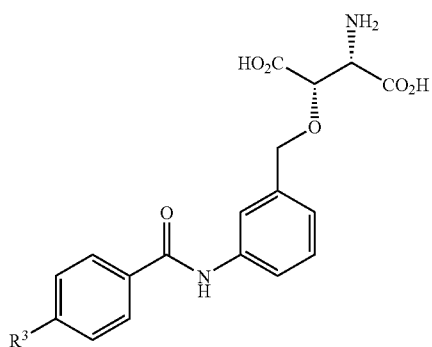

(3)

These compounds contribute to the development of a method of specifically detecting L-glutamate transporter function. The development of such a method is expected as applicable to the treatment for neuronal disorders and neurodegenerative diseases such as epilepsy, Huntington's disease, amyotrophic lateral sclerosis (ALS) and Alzheimer's disease.

Related Art

It is known that L-glutamic acid, which is an excitatory neurotransmitter in mammalian central nervous systems, rapidly induces neural transmission between synapses and, moreover, participates in complicated higher order physiological processes such as memory and learning. Excitatory neurotransmission between synapses starts with a release of glutamate from presynapses and ends with a rapid uptake of the glutamate from synaptic clefts by high affinity glutamate transporter in nerve endings and glial cells (Attwell, D. and Nicholls, D., TIPS 68-74, 1991).

It is reported that sodium-dependent glutamate uptake activity is lowered in the brains of some patients suffering from certain hereditary neurodegenerative diseases (Rothstein, J. D. et al., N. Eng. J. Med 326, 1464-1468, 1992). The present inventors have found that the expression level of glutamate transporter gene is changed in rats with drug dependence and the symptoms are worsened by inhibiting the transporter (Ozawa, T. et al., Eur. J. Neurosci., 19, 221-226, 2004; Sekiya, Y., et al., Eur. J. Pharmacol., 485, 201-210, 2004). Therefore, the expression and inhibition of the glutamate transporter function have attracted great attention in the context of these diseases and drug dependence. For example, it appears that glutamate transporter dysfunction is a factor causative of neuronal disorders such as epilepsy, Huntington's disease, amyotrophic lateral sclerosis (ALS), Alzheimer's disease and drug dependence.

To study the relationship between the physiological role of glutamate transporters and pathological conditions, it is highly important to use a selective inhibitor (Bridges, R. J. et al., Curr Pharm Des 5: 363-379, 1999; Balcar, V. J., Biol Pharm Bull 25: 291-301, 2002; Campiani, G. et al., J Med Chem 44:2507-2510, 2003; Shigeri, Y. et al., Brain Res. Rev. 45, 250-265, 2004). Development of a method of specifically detecting the function of glutamate transporters largely contributes to the clarification of the relationship between these pathological conditions and the transporter function.

From this viewpoint, the present inventors have reported that β-hydroxyaspartic acid derivatives having a substituent at the β-position exhibit an inhibitory effect against the glutamate uptake by all of excitatory amino acid transporter subtypes EAAT1 to EAAT5 (Lebrun, B. et al., J. Biol. Chem. 272, 20336-20339, 1997; Shimamoto, K. et al., Mol. Pharmacol. 53, 195-201, 1998; Shigeri, Y. et al., J. Neurochem. 79, 297-302, 2001). It has also been reported that, among all these derivatives, threo-β-benzyloxyaspartic acid (TBOA) serves as a blocker for all EAAT subtypes and thus inhibits not only the glutamate uptake but also the sodium ion influx and the glutamate efflux caused by hetero exchange reactions (Chatton, J-Y. et al., Brain Res. 893, 46-52, 2001; Anderson, C. M. et al., J. Neurochem., 79, 1207-1216, 2001). The present inventors have further found that the affinity of TBOA is remarkably elevated by introducing a substituent on its benzene ring (Shimamoto et al., Mol. Pharmacol., 65, 1008-1015 (2004)).

By radio-labeling such a selective and high-affinity ligand of the transporter, a specific binding even in a trace amount could be detected. Thus, such radio-labeling would bring about a significant contribution in the field of drug searching based on binding experiments to screen for novel ligands and isolate novel proteins. It would also be expected that the distribution and expression of glutamate transporter and the level of its ability to take up glutamate could be visualized with the use of autoradiography and positoron emission tomography (PET) techniques. However, no compound usable in the detection of specific bindings or the visualizing techniques has been known from the viewpoint of satisfactory affinity and selectivity.

REFERENCES

1. Attwell, D. and Nicholls, D., TIPS 68-74, 1991
2. Rothstein, J. D. et al., N. Eng. J. Med 326, 1464-1468, 1992
3. Ozawa, T. et al., Eur. J. Neurosci., 19, 221-226, 2004
4. Sekiya, Y., et al., Eur. J. Pharmacol., 485, 201-210, 2004
5. Bridges, R. J. et al., Curr Pharm Des 5: 363-379, 1999
6. Balcar, V. J., Biol Pharm Bull 25: 291-301, 2002
7. Campiani, G. et al., J Med Chem 44:2507-2510, 2003
8. Shigeri, Y. et al., Brain Res. Rev. 45, 250-265, 2004
9. Lebrun, B. et al., J. Biol. Chem. 272, 20336-20339, 1997
10. Shimamoto, K. et al., Mol. Pharmacol. 53, 195-201, 1998
11. Shigeri, Y. et al., J. Neurochem. 79, 297-302, 2001
12. Chatton, J-Y. et al., Brain Res. 893, 46-52, 2001
13. Anderson, C. M. et al., J. Neurochem., 79, 1207-1216, 2001
14. Shimamoto et al., Mol. Pharmacol., 65, 1008-1015 (2004)

DISCLOSURE OF THE INVENTION

The present invention provides a radiolabeled compound which is highly selective and potent for glutamate transporter and usable as a ligand and/or an inhibitor in the specific detection of glutamate transporter, and a method of producing the same.

The present invention also provides a precursor compound for producing the above-described radiolabeled compound.

BRIEF DESCRIPTION OF THE DRAWINGS

FIG. 7 shows the saturation binding of ($^3$H)Et-BzA-TBOA to EAAT2, EAAT4, or EAAT5 expressed on COS-1 cells.

FIG. 8 shows the Scatchard analysis of ($^3$H)Et-BzA-TBOA to EAAT2, EAAT4, or EAAT5 expressed on COS-1 cells.

EMBODIMENTS OF THE INVENTION

Figure 1:
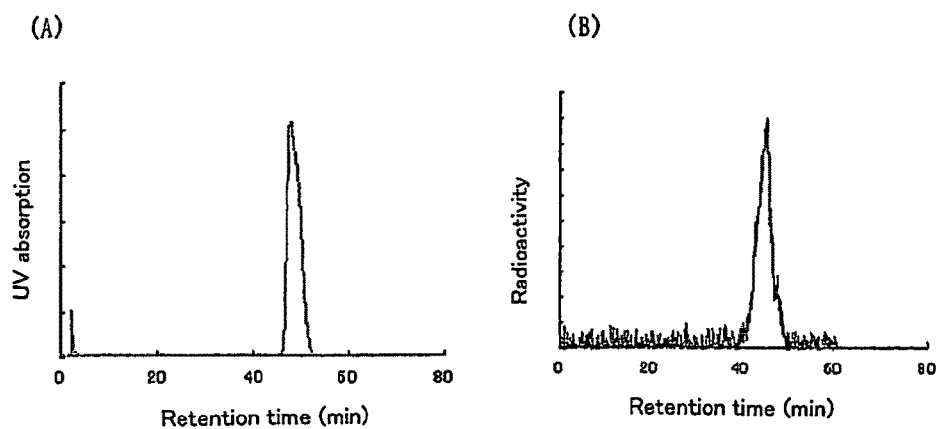
FIG. 1(A) shows a high-performance liquid chromatogram of 1-BzA-TBOA.
FIG. 1(B) shows a radiochromatogram of [$^{125}$I]I-BzA-TBOA.

The present inventors focused on the high affinity of TBOA (threo-β-benzyloxyaspartic acid) derivatives and attempted to synthesize corresponding derivatives having a radioactive substituent on the benzene ring of TBOA in order to obtain derivatives which can be used for specifically detecting the glutamate transporter function. As a result of intensive studies, they have found that selective detection by radioactivity of a binding with glutamate transporter is achievable by introducing a substituent which contains a radioactive atom(s) onto the benzoyl group of a benzoylamido-substituted TBOA (X-BzA-TBOA), which is a high-affinity blocker, binding to glutamate transporter, thereby accomplishing the present invention.

Accordingly, the present invention provides a derivative of 3-[3-(benzoylamido)benzyloxy]aspartic acid having a radioactive group as a substituent on the benzoyl group, which is represented by the following formula (1):

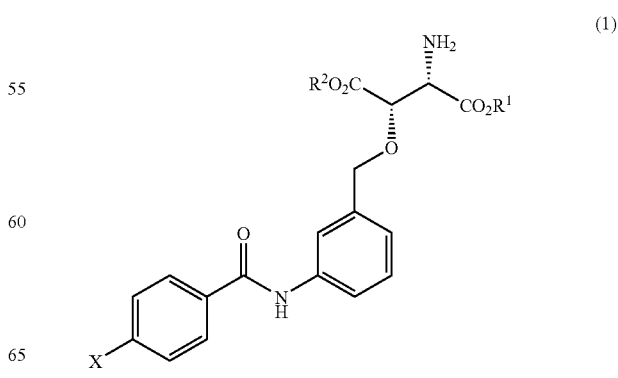

wherein X represents a substituent containing a radioactive atom(s) which is selected from a straight or branched lower aliphatic alkyl group, a hydroxyl group, a straight or branched lower aliphatic alkoxy group, an amino group, a straight or branched lower aliphatic acylamido group, a halogen atom and a straight or branched lower aliphatic haloalkyl group; and $R^1$ and $R^2$ each represents a hydrogen atom, a straight or branched lower aliphatic alkyl group or an acetoxymethyl group; or an ester or salt thereof, as a ligand for specifically detecting the glutamate transporter function.

Examples of the radioactive atom possibly contained in the group X in the compound of the formula (1) include $^{125}I$, $^{14}C$, $^{3}H$, $^{123}I$, $^{18}F$, $^{11}C$, $^{13}N$ and $^{15}O$. Specific examples of X having these atoms include methyl group, ethyl group, hydroxyl group, methoxy group, ethoxy group, amino group, acetamido group, halogen atoms, halomethyl groups, haloethyl groups and so on.

It is estimated that, when the compound according to the present invention exerts its inhibitory activity, the carboxylate moiety is in the free state ($R^1$=$R^2$=H). By taking the in vivo kinetics and the blood-brain barrier permeability into consideration, it is possible in some cases to convert both or one of $R^1$ and $R^2$ in the formula (1) into an ester. Examples of the ester include methyl, ethyl, n-propyl, i-propyl, n-butyl, s-butyl, t-butyl and acetoxymethyl esters. These esters are all included in the scope of the present invention.

A salt of the compound according to the present invention can be prepared by a commonly employed method. Examples of such salts include alkali metal salts such as sodium salt and potassium salt, alkaline earth metal salts such as calcium salt, ammonium salts and so on. These salts are all included in the scope of the present invention. It is also possible to prepare a salt by using a commonly employed acid. Examples of such salts include inorganic acid salts such as hydrochloride and sulfate, organic acid salts such as acetate, citrate and trifluoracetate and so on. These salts are all included in the scope of the present invention too.

TBOA occurs as four stereoisomers and the (2S,3S) compound shows the strongest activity among them. The substituent on the benzoyl ring may be located at three positions, i.e., ortho-, meta- and para-positions. Studies on the structure-activity-relationship of these compounds clarified that the para-compound shows the strongest activity. Therefore, in the following synthesis scheme the introduction of a radioactive substituent is shown by taking compounds having a (2S,3S)-configuration in the aspartic acid and having the substituent at the para-position on the benzoyl, though all isomers having different substitution or configuration manners are included in the scope of the present invention.

The compound of the formula (1) according to the present invention can be produced by an electrophilic substitution reaction between the leaving group of a compound represented by the formula (2) and a radioactive atom(s):

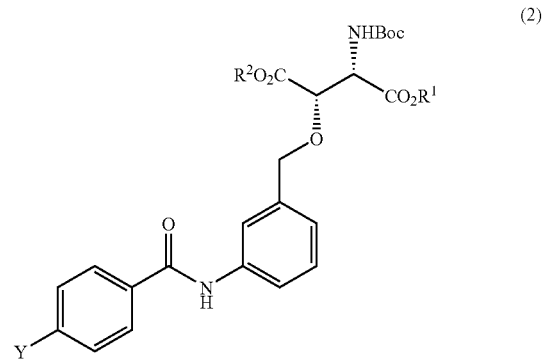

(2)

wherein $R^1$ and $R^2$ each represents a hydrogen atom, a straight or branched lower aliphatic alkyl group or an acetoxymethyl group; Y represents a leaving group to undergo a substitution reaction which is an organometallic group, a halogen atom, a diazo group, a diazonium group, a trialkylammonium group or a nitro group; and Boc represents a t-butoxycarbonyl group.

In the case where Y is an organometallic group, examples thereof include tin, thalium, mercury, silicon, aluminum and boron. Examples of an organic substituent on the metal include lower straight alkyl groups, acetyl group and trifluoroacetyl group (Baldwin R. M., Appl. Radiat. Isot. 37, 817-821, 1986).

For example, a compound of the formula (1) wherein X is $^{125}I$ and $R^1$ and $R^2$ are hydrogen atoms ($^{125}I$-BzA-TBOA) can be synthesized by starting with a precursor of the formula (2) wherein Y is organotin (compound 3) and [$^{125}I$]NaI in accordance with, for example, the following scheme.

(Scheme 1)

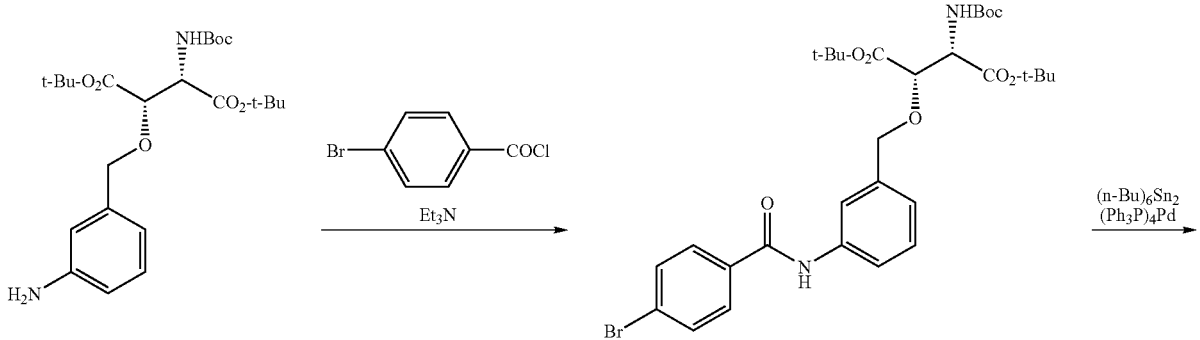

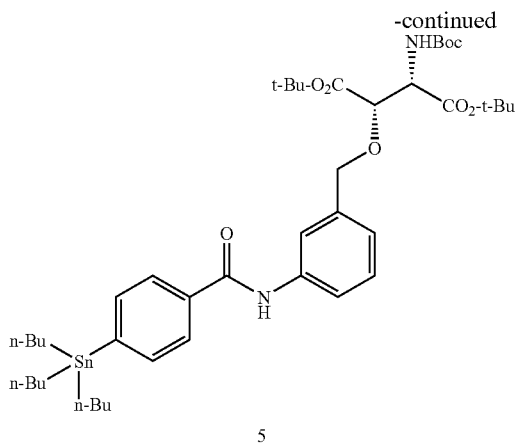

5

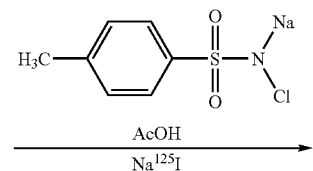

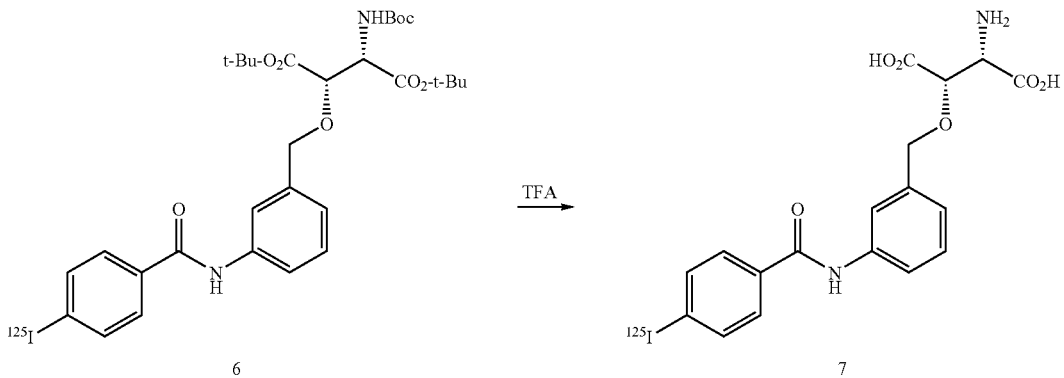

Namely, protected (2S,3S)-3-[3-(4-bromobenzoyl)benzyloxy]aspartic acid (4), which is obtained form a known compound (3) by the same method as in synthesizing TFB-TBOA (Japanese Patent Application 2003-507101 (PCT/JP02/06286, WO03/00698), Shimamoto, K. et al., Mol. Pharmacol., 65, 1008-1015 (2004)), is treated with tributyltin dimer in the presence of a palladium catalyst to perform a substitution reaction. Thus a tin compound (5) is obtained. Next, the compound (5) is reacted with radioactive sodium iodide in the presence of an oxidizing agent and acetic acid. As a result, radioactive iodine is introduced by an oxidative tin-iodine exchange reaction to give a compound (6). By adding trifluoroacetic acid, Boc group and t-butyl ester group are removed to give the target compound (7).

A compound having $^{123}I$ in place of $^{125}I$ can be obtained by the same oxidative tin-iodine exchange reaction. It is also known that a compound wherein Y is a tributylsilyl group, tris(trifluoroacetoxy)thallium or tris(trifluoroacetoxy)mercury undergoes the same substitution reaction with iodine.

It is also possible to obtain an ester derivative by preliminarily introducing desired esters into $R^1$ and $R^2$ of the compound (4).

There has been known a method which comprises treating a tin compound with radioactive methyl iodide in the presence of a palladium catalyst and copper chloride to thereby introduce a methyl group (Suzuki, M. et al., Chem. Eur. J. 3, 2039, 1997; Suzuki, M. et al., Tetrahedron, 56, 8263, 2000). Thus, a compound (9) can be synthesized from the compound (5) in the same manner (Scheme 2).

(Scheme 2)

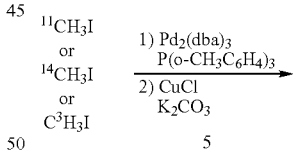

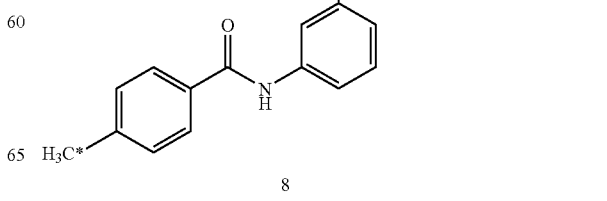

-continued

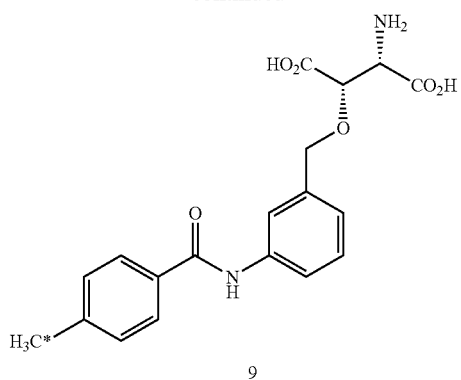

9

*CH₃: labeled methyl group

-continued

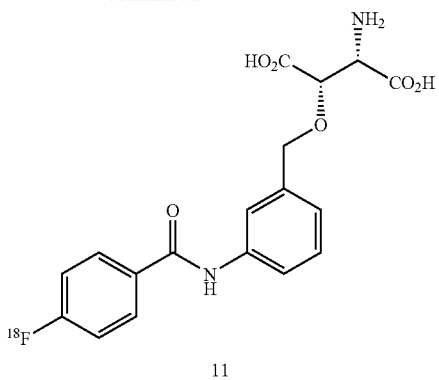

11

As for an $^{18}$F-substituted compound (11), [$^{18}$F]-4-fluorobenzoic acid is known (Murakami, Y. et al., J. Labelled Compd. Radiopharm., 45, 2002, 1219-1228, 2002), which may thus be reacted with the compound (3) (Scheme 3) or a substitution with [$^{18}$F]KF can be carried out by using a nitro compound (12) (Shimamoto et al., Mol. Pharmacol., 65, 1008-1015 (2004)) as a precursor as reported in the above document (Scheme 4).

(Scheme 4)

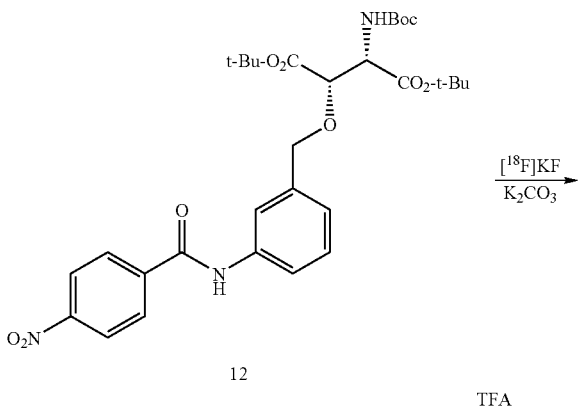

12

10 $\xrightarrow{\text{TFA}}$ 11

The compound of formula (1) wherein X represents a tritium-containing alkyl group can be produced by the addition of tritium gas to a compound represented by the formula (3) wherein R³ is as defined above:

(3)

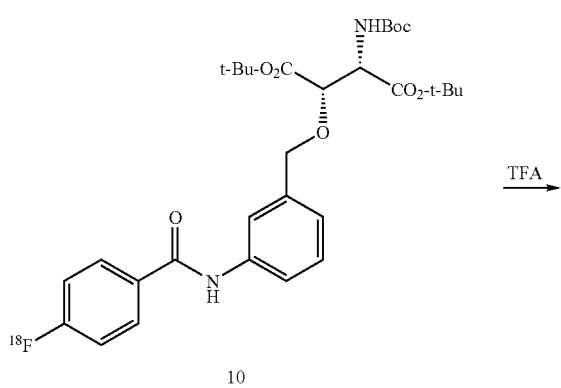

For example, the tritium-containing ethyl compound (15: [³H]Et-BzA-TBOA) represented by the formula (1) wherein X is C₂H₃T₂ group and R¹ and R² are hydrogen atoms can be synthesized from a precursor of the formula (3) wherein R3 is vinyl group as shown in scheme 5.

(Scheme 3)

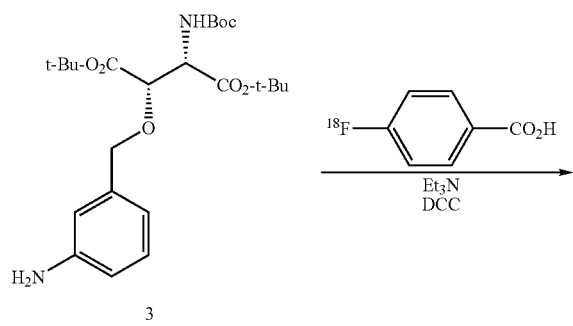

3

$\xrightarrow[\text{DCC}]{\text{Et}_3\text{N}}$ $^{18}$F-⟨benzene⟩-CO₂H

[image of compound 10 with $^{18}$F label]

10

$\xrightarrow{\text{TFA}}$ (Scheme 5)

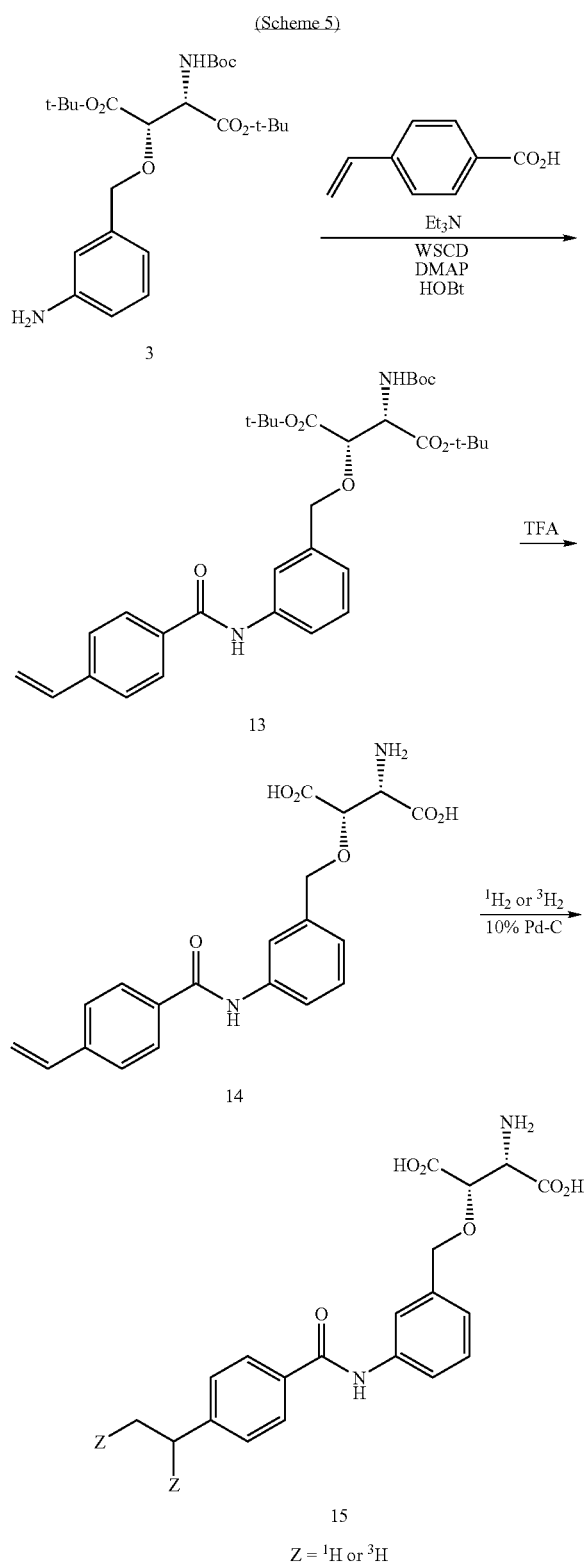

It has been found that the compound according to the present invention shows a high affinity as well as an inhibitory effect on glutamate transporter. The fact that the compound according to the present invention binds to and/or inhibits the glutamate transporter with a high affinity is confirmed by using a corresponding non-radioactive compound.

That is to say, the inhibitory activity of $^{125}$I-BzA-TBOA or $^{123}$I-BzA-TBOA is assayed as the ability to inhibit the uptake of $^{14}$C-labeled glutamic acid by human excitatory amino acid transporters EAAT2 and EAAT3 stably expressed in MDCK (Madin-Darby canine kidney) cells with the use of $^{127}$I-BzA-TBOA. In monitoring kinetics in vivo after intravenous injection into rats or carrying out binding experiments in brain synaptic membrane preparations with the use of a radioactive compound ($^{125}$I-BzA-TBOA), a transporter-specific binding can be detected by tracing the radioactivity. Similarly, Et-BzA-TBOA inhibited EAAT2 or EAAT3 with almost the same potency as I-BzA-TBOA. Specific binding of ($^3$H)Et-BzA-TBOA also can be detected by tracing the radioactivity.

Although F-BzA-TBOA shows a somewhat lower affinity for glutamate transporter than I-BzA-TBOA, F-BzA-TBOA shows an $IC_{50}$ at the several ten nM order and, therefore, is expected to have a similar specific bind ability.

Therefore, the present invention further provides a method of examining the distribution and/or expression of glutamate transporter and/or the glutamate uptake level in a biological sample. The method according to the present invention comprises: a) contacting the biological sample with a compound as claimed in claim 1, an inhibitor as claimed in claim 7 or a ligand as claimed in claim 8; b) examining the presence or absence of the compound as claimed in claim 1, the inhibitor as claimed in claim 7 or the ligand as claimed in claim 8 having bound specifically to the biological sample with the use of the radioactivity as an indication; and c) in the case where the specific binding is observed in the above step b), estimating that the glutamate transporter is distributed or expressed in the biological sample or the corresponding part participates in the glutamate uptake. Those skilled in the art once provided with the ligand according to the present invention can carry out the method according to the present invention by exploiting conventional techniques.

ADVANTAGES OF THE INVENTION

It is expected that the compounds according to the present invention enable visualization of the distribution and/or expression of glutamate transporter and/or the ability of the transporter to take up glutamate through binding experiments, autoradiography and PET, and so on. Therefore, these compounds are expected to be useful for clarifying the pathological conditions of neurodegenerative diseases such as epilepsy, Huntington's disease, amyotrophic lateral sclerosis (ALS), Alzheimer's disease and drug dependence seemingly caused by dysfunction of glutamate transporter.

Furthermore, the radiolabeled ligands according to the present invention, being highly selective and affinitive to glutamate transporter, are capable of detecting the specific binding occurring even in a trace level. Thus, these ligands are also expected to contribute, by way of binding experiments, to drug development via screening of novel ligands and isolation of proteins.

EXAMPLES (A) Synthesis of [$^{125}$I]I-BzA-TBOA and its Non-Radioactive Analog (1) Synthesis of (2S,3S)-3-[3-(4-[$^{125}$I]iodobenzoylamino)benzyloxy]aspartic acid (7: [$^{125}$I]I-BzA-TBOA)

(2S,3S)—N-t-butoxycarbonyl-3-[3-(4-bromobenzoylamino)benzyloxy]aspartic acid di-t-butyl ester (4)

200 mg (0.42 mmol) of the known amino compound (3) was dissolved in 4 ml of chloroform. After adding 4-bromobenzoyl chloride (110 mg, 0.50 mmol) and triethylamine (120 μl, 0.84 mmol) thereto, the obtained mixture was stirred for 30 minutes. Then a saturated aqueous solution of sodium hydrogencarbonate was added to thereby cease the reaction. The reaction mixture was extracted with ether and the organic layer was washed successively with water, a 5% aqueous solution of citric acid and water. After drying over magnesium sulfate, the solvent was distilled off. The residue was purified by silica gel column chromatography (ether/hexane=1/1) to thereby give 283 mg (100%) of the title compound. Oily product; $[\alpha]_D$-6.3° (c 0.65, CHCl$_3$); $^1$H NMR (CDCl$_3$, 400 MHz); ™1.41 (s, 9 H), 1.43 (s, 9 H), 1.49 (s, 9 H), 4.42 (d, 1 H, J=11.5 Hz), 4.44 (d, 1 H, J=2.5 Hz), 4.75 (dd, 1 H, J=2.5, 10.5 Hz), 4.82 (d, 1 H, J=11.5 Hz), 5.26 (d, 1 H, J=10.5 Hz), 7.10 (d, 1 H, J=7.5 Hz), 7.34 (t, 1 H, J=7.5 Hz), 7.45 (s, 1 H), 7.64 (d, 2 H, J=8.5 Hz), 7.74 (m, 1 H), 7.74 (d, 2 H, J=8.5 Hz), 7.81 (s, 1 H).

(2S,3S)-N-t-butoxycarbonyl-3-{3-[4-(tri-n-butylstannyl)benzoylamino]benzyloxy}aspartic acid di-t-butyl ester (5)

The bromo compound (4) (25 mg, 0.038 mmol), hexa-n-butyl ditin (48 μl, 0.095 mmol) and triethylamine (10 μl, 0.076 mmol) were dissolved in dry toluene. After adding tetrakis(triphenylphosphine)palladium (2.2 mg, 0.0019 mmol), the obtained mixture was heated under reflux in an argon atmosphere for 2 hours. After cooling by allowing to stand, the reaction solution was subjected to silica gel column chromatography (hexane to ether/hexane=1/3) to give 17 mg (52%) of the title compound. Oily product; $[\alpha]_D$ -5.4° (c 0.58, CHCl$_3$); $^1$H NMR (CDCl$_3$, 400 MHz); δ 0.90 (t, 9 H, J=7.5 Hz), 1.10 (t, 6 H, J=7.5 Hz), 1.34 (m, 6 H), 1.41 (s, 9 H), 1.43 (s, 9 H), 1.49 (s, 9 H), 1.55 (m, 6 H), 4.42 (d, 1 H, J=11.5 Hz), 4.45 (d, 1 H, J=2.0 Hz), 4.65 (dd, 1 H, J=2.5, 10.5 Hz), 4.81 (d, 1 H, J=11.5 Hz), 5.25 (d, 1 H, J=10.5 Hz), 7.19 (d, 1 H, J=7.5 Hz), 7.34 (t, 1 H, J=7.5 Hz), 7.46 (s, 1 H), 7.60 (d, 2 H, J=7.5 Hz), 7.74 (d, 1 H., J=8.0 Hz), 7.78 (d, 2 H, J=7.5 Hz), 7.81 (s, 1 H).

(2S,3S)-3-[3-(4-[$^{125}$I]iodobenzoylamino)benzyloxy] aspartic acid (7)

To 1.5 μl of an aqueous solution of [$^{125}$I]NaI were added 10 μl of a solution of the tin compound (5) (10 mg/ml) in ethanol, 100 μl of 1.25% acetic acid and 50 μl of an aqueous Chloramine T solution (2 mg/ml). After reacting at room temperature for 10 minutes, the reaction mixture was extracted with 2 ml of ethyl acetate. After distilling off the organic layer under reduced pressure, 2001 portions of TFA and chloroform were added to the residue and the mixture was reacted at room temperature overnight. After distilling off TFA/chloroform under reduced pressure, the residue was mixed with methanol, dissolved therein and subjected to reverse phase HPLC to purify the title compound. HPLC conditions; column: Cosmosil 5C18-AR-300 4.6×150 mm (manufactured by Nacalai Tesque, Inc.), mobile phase: 0.1% aqueous TFA solution/methanol=65/35, flow rate: 1.0 ml/min, retention time of compound (7): 45 min. Based on the high-performance liquid chromatogram shown in FIG. 1, the radiochemical yield and the radiochemical purity were estimated respectively to be 56% and 95% or higher.

(2) Measurement of Octanol-Water Partition Coefficient (Log P)

Equal amounts of octanol and a phosphate buffer were mixed together and [$^{125}$I]I-BzA-TBOA was added thereto. After repeatedly shaking for 1 minute and allowing to stand for 1 minute three times, the mixture was allowed to stand for 20 minutes. After repeating this procedure three times, it was centrifuged (1,000×g, 10 min, 4° C.) and the radioactivity of each layer was measured. Thus, the partition coefficient was calculated (Table 1).

TABLE 1

| Octanol/water partition coefficient (Log P) of [$^{125}$I]I-BzA-TBOA | | | |
|---|---|---|---|
| PH 3.0 | PH 7.0 | PH 7.4 | PH 8.0 |
| 0.641 ± 0.006 | −0.821 ± 0.003 | −0.849 ± 0.006 | −0.936 ± 0.007 |

Each value is expressed in mean ± S.D.

(3) Synthesis of Non-Radioactive (2S,3S)-3-[3-(4-iodobenzoylamino)benzyloxy]aspartic acid (I-BzA-TBOA)

(2S,3S)—N-tert-butoxycarbonyl-3-[3-(4-iodobenzoylamino)benzyloxy]aspartic acid di-t-butyl ester 100 mg (0.21 mmol) of the amino compound (3) was dissolved in 2 ml of chloroform. After adding 4-iodobenzoyl chloride (67 mg, 0.25 mmol) and triethylamine (60 μl, 0.42 mmol) thereto, the obtained mixture was stirred for 30 minutes. Then a saturated aqueous solution of sodium hydrogencarbonate was added to thereby cease the reaction. The reaction mixture was extracted with ether and the organic layer was washed successively with water, a 5% aqueous solution of citric acid and water. After drying over magnesium sulfate, the solvent was distilled off. The residue was purified by silica gel column chromatography (ether/hexane=1/1) to thereby give 147 mg (100%) of the title compound. Oily product; $[\alpha]_D$ −5.2° (c 0.52, CHCl$_3$); $^1$H NMR (CDCl$_3$, 400 MHz); δ 1.41 (s, 9 H), 1.42 (s, 9 H), 1.49 (s, 9 H), 4.42 (d, 1 H, J=11.5 Hz), 4.44 (d, 1 H, J=2.5 Hz), 4.75 (dd, 1 H, J=2.5, 10.5 Hz), 4.80 (d, 1 H, J=11.5 Hz), 5.26 (d, 1 H, J=10.5 Hz), 7.09 (d, 1 H, J=7.5 Hz), 7.33 (t, 1 H, J=7.5 Hz), 7.45 (s, 1 H), 7.60 (d, 2 H, J=8.5 Hz), 7.72 (m, 1 H), 7.84 (d, 2 H, J=8.5 Hz), 7.90 (s, 1 H).

(2S,3S)-3-[3-(4-iodobenzoylamino)benzyloxy]aspartic acid (I-BzA-TBOA)

Protected I-BzA-TBOA (120 mg, 0.17 mmol) was dissolved in 1 ml of chloroform. After adding 1 ml of TFA, the obtained mixture was stirred for 24 hours. Then the solvent was distilled off and water was added to the residue followed by repeated freeze-drying. Thus, 78 mg (76%) of the title compound was obtained. Amorphous product; $[\alpha]_D$ −37.7° (c 0.34, CHCl$_3$); $^1$H NMR (CDCl$_3$, 400 MHz); ™4.30 (d, 1 H, J=5.0 Hz), 4.45 (d, 1 H, J=11.0 Hz), 4.68 (d, 1 H, J=11.0 Hz), 7.14 (d, 1 H, J=7.5 Hz), 7.30 (t, 1 H, J=8.0 Hz), 7.59 (s, 1 H), 7.64 (d, 1 H, J=8.5 Hz), 7.67 (d, 2 H, J=7.5 Hz), 7.86 (d, 2 H, J=7.5 Hz).

(4) Synthesis of [$^3$H]Et-BzA-TBOA (2S,3S)—N-t-butoxycarbonyl-3-[3-(4-vinylbenzoylamino)benzyloxy]aspartic acid di-t-butyl ester (13)

100 mg (0.21 mmol) of the known compound (3) was dissolved in DMF (5 ml). After adding 64 mg (0.42 mmol) of 4-vinylbenzoic acid, 99 mg (0.51 mmol) of 1-ethyl-3-(3-dimethylaminopropyl)carbodiimide HCl salt (WSCD), 60 μl (0.43 mmol) of triethylamine, 7.9 mg (0.06 mmol) of 4-N,N-dimethylaminopyridine (DMAP) and 29 mg (0.21 mmol) of 1-hydroxybenzotriazole (HOBt) thereto, the obtained mixture was stirred for 30 minutes at room temperature. Then a saturated aqueous solution of sodium hydrogencarbonate was added to thereby cease the reaction. The reaction mixture was extracted with ether and the organic layer was washed successively with water, a 5% aqueous solution of citric acid and water. After drying over magnesium sulfate, the solvent was distilled off. The residue was purified by silica gel column chromatography (ether/hexane=1/1) to thereby give 115 mg (90%) of the title compound. Oily product; 400 MHz $^1$H-NMR (CDCl$_3$): 1.41 (s, 9 H), 1.42 (s, 9 H), 1.49 (s, 9 H), 4.41 (d, 1 H, J=11.5 Hz), 4.44 (d, 2 H, J=2.5 Hz), 4.75 (dd, 1 H, J=2.5, 10.5 Hz), 4.80 (d, 1 H, J=11.5 Hz), 5.27 (d, 1 H, J=10.5 Hz), 5.38 (d, 1 H, J=11.0 Hz), 5.87 (d, 1 H, J=17.5 Hz), 6.76 (dd, 1 H, J=11.0, 17.5 Hz), 7.09 (d, 1 H, J=7.5 Hz), 7.13 (t, 1 H, J=7.8 Hz), 7.46 (s, 1 H), 7.50 (d, 2 H, J=8.0 Hz), 7.75 (d, 1 H, J=7.8 Hz), 7.82 (d, 2 H, J=8.0 Hz), 7.90 (s, 1 H).

(2S,3S)-3-[3-(4-vinylbenzoylamino)benzyloxy]aspartate (14)

36 mg (0.06 mmol) of the compound 13 was dissolved in 1 ml of chloroform. After adding 1 ml of TFA thereto, the obtained mixture was stirred for 18 hours. Then the solvent was distilled off and water was added to the residue followed by repeated freeze-drying. Thus, 25 mg (83%) of the title compound was obtained. Amorphous product; 400 MHz $^1$H-NMR (AcOD-d$_4$): 4.60 (1 H, d, J=11.5 Hz), 4.63 (0.1 H, d, J=2.5 Hz), 4.80 (1 H, d, J=2.5 Hz), 4.83 (1 H, d, J=11.5 Hz), 5.40 (1 H, d, J=11.0 Hz), 5.94 (1 H, d, J=17.5 Hz), 6.82 (1 H, dd, J=11.0, 17.5 Hz), 7.16 (1 H, d, J=8.0 Hz), 7.36 (1 H, t, J=8.0 Hz), 7.57 (2 H, d, J=8.0 Hz), 7.67 (1 H, s), 7.77 (1 H, d, J=8.0 Hz), 7.97 (2 H, d, J=8.0 Hz).

(2S,3S)-3-[3-(4-ethylbenzoylamino)benzyloxy]aspartate (15) (Et-Bza-Tboa)

10 mg (0.02 mmol) of TFA salt of the vinyl compound (14) was dissolved in a solvent mixture comprising 2 ml of acetic acid with 1 ml of water. After adding 5 mg of catalyst (10% Pd—C), the obtained mixture was stirred under atmospheric pressure in a hydrogen atmosphere at room temperature for 3 hours. Then the catalyst was filtered off and the filtrate was concentrated and repeatedly freeze-dried from water three times to give 7.5 mg of the target product (2). Yield: 84%. Amorphous product; 400 MHz $^1$H-NMR (AcOD-d$_4$): 1.27 (3 H, t, J=7.5 Hz), 2.74 (2 H, q, J=7.5 Hz), 4.58 (2 H, m), 4.82 (2H, m), 7.17 (1 H, d, J=7.0 Hz), 7.28 (1 H) 7.28 (2 H, d, J=7.5 Hz), 7.62 (1 H, s), 7.79 (1 H, d, J=8.0 Hz), 7.86 (2H, d, J=7.5 Hz).

A tritium-labeled compound can be synthesized by using tritium gas instead of the hydrogen gas in the above reaction.

Figure 5:
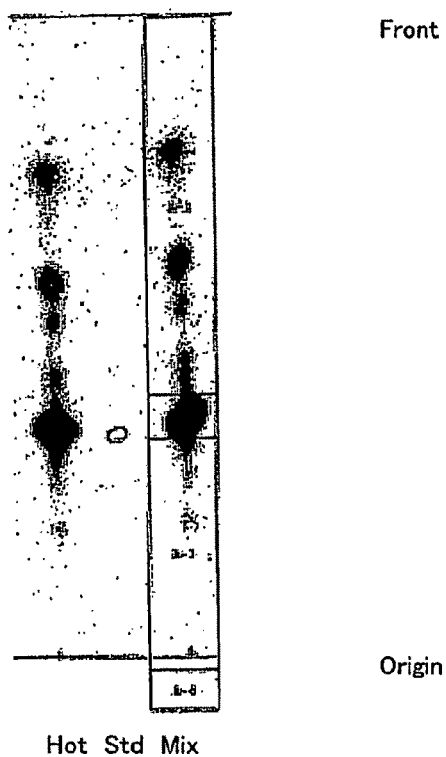
FIG. 5 shows a silica gel thin layer chromatogram for examining the purity of a tritium-labeled compound ([$^3$H]Et-BzA-TBOA).

FIG. 5 shows thin layer chromatogram on silica gel for examining the purity of the tritium-labeled compound.

The development conditions employed in the silica gel thin layer chromatography were as follows.
Medium: Silica gel 60 F254 (Merck, thickness 0.25 mm)
Solvent: 1-butanol/acetic acid/water (4/1/2)
Detection: UV 254 nm
Imaging plate: BAS-MS2040 (Fuji Photo Film)
Instrument: BIO-IMAGING ANALYZER BAS2000 (Fuji Photo Film)

According to this calibration, the radiochemical purity was estimated to be 97.1%.

Figure 6:
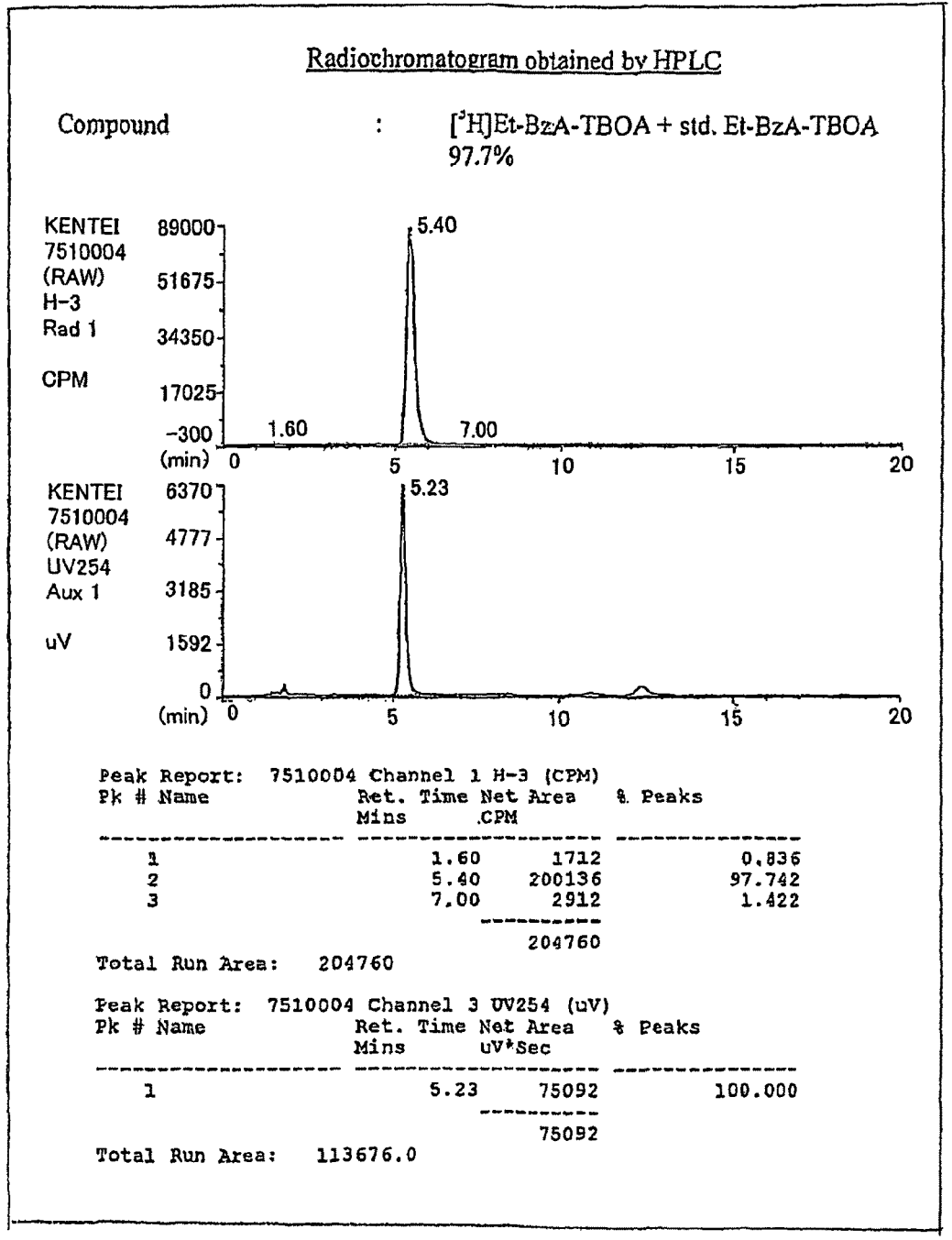
FIG. 6 shows a high performance liquid chromatogram for examining the purity of a tritium-labeled compound ([$^3$H]Et-BzA-TBOA).

FIG. 6 shows high-performance liquid chromatogram for examining the purity of the tritium-labeled compound.

The elution conditions employed in the HPLC were as follows.
Column: Cosmosil 5C18-MS-II, 4.6 mm I.D.×150 cm (NACALAI TESQUE)
Mobile phase: acetonitrile/water (3/7) containing 0.1% TFA
Flow rate: 1 ml/min
Detection: UV 254 nm
Radiodetection: 525TR (PerkinElmer)
Scintillation cocktail: FLO-SCINT II (Perkin Elmer)

According to this calibration, the radiochemical purity was estimated to be 97.7%.

(B) Assay of Biological Activity and Detection of Specific Binding (1) Assay of Glutamate Transporter Inhibitory Activity of X-BzA-TBOA In accordance with a known method (Shimamoto, K. et al., Mol. Pharmacol. 53, 195-201, 1998; Bioorg. Med. Chem. Lett. 10, 2407-2410, 2000), the inhibitory activity was assayed as the ability to inhibit the uptake of [$^{14}$C]-glutamic acid by human EAAT2 and EAAT3 stably expressed in MDCK (Madin-Darby canine kidney) cells or transiently expressed in COS-1 cells. The glutamate uptake activity was assayed by incubating a mixture of 1 μM of L-[$^{14}$C]-glutamic acid with a sample compound at a predetermined concentration for 12 minutes, lysing the cells and then measuring the radioactivity incorporated into the cells with a liquid scintillator. The amount of uptake was expressed in percentage by referring the amount of uptake in the absence of a test compound (i.e., the buffer alone) as 100% and referring the amount of uptake in a sodium-free solution as 0%. Table 2 shows IC$_{50}$ data thus determined.

TABLE 2

Inhibition of glutamate uptake by I-BzA-TBOA and comparative compounds

| | EAAT2 IC$_{50}$ (nM) | EAAT3 IC$_{50}$ (nM) |
|---|---|---|
| L-TBOA | 1300 ± 120 | 1300 ± 120 |
| TFB-TBOA | 1.9 ± 0.10 | 28 ± 1.8 |
| I-BzA-TBOA | 4.8 ± 0.32 | 56 ± 1.8 |
| F-BzA-TBOA | 22 ± 2.7 | 473 ± 13 |
| Et-BzA-TBOA | 3.2 ± 0.3 | 88 ± 4.8 |

(2) Measurement of In Vivo Kinetics Using [$^{125}$I]I-BzA-TBOA

Figure 2:
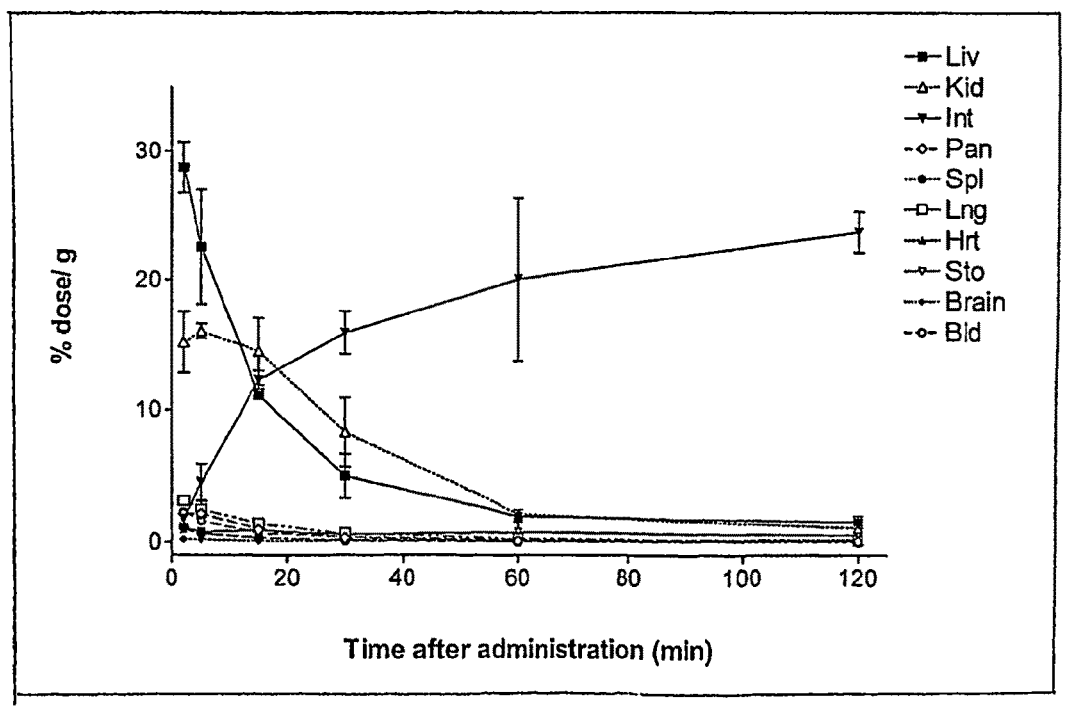
FIG. 2 is a graph showing the radioactivity distribution in organs after administering [$^{125}$I]I-BzA-TBOA to mice, wherein Liv stands for liver, Kid stands for kidney, Int stands for intestines, Pan stands for pancreas, Spl stands for spleen, Lng stands for lung, Hrt stands for heart, Sto stands for stomach, Brain stands for brain and Bld stands for blood.

[$^{125}$I]I-BzA-TBOA (about 1 μCi) was injected via tail vein into male ddy mice (29 to 31 g) aged 6 weeks. After 2, 5, 15, 30, 60 and 120 minutes, the animals were sacrificed. Then, liver, kidney, intestine, spleen, pancreas, lung, heart, stomach, brain and blood were collected from the animals and weighed and the radioactivity of each organ was measured. Table 3 and FIG. 2 show the results.

TABLE 3

Biodistribution of radioactivity after intravenous injection of [$^{125}$I]I-BzA-TBOA in mice

| Organ | Time after administration | | | | | |
|---|---|---|---|---|---|---|
| | 2 min | 5 min | 15 min | 30 min | 1 hr | 2 hr |
| Liver | 28.71 ± 1.97 | 22.52 ± 4.43 | 11.11 ± 0.24 | 4.96 ± 1.65 | 1.95 ± 0.46 | 1.50 ± 0.43 |
| Kidney | 15.17 ± 2.34 | 16.02 ± 0.57 | 14.47 ± 2.59 | 8.29 ± 2.63 | 2.08 ± 0.15 | 1.03 ± 0.23 |
| Intestine | 1.76 ± 0.15 | 4.51 ± 1.36 | 12.28 ± 0.72 | 15.91 ± 1.65 | 20.05 ± 6.29 | 23.69 ± 1.58 |
| Pancreas | 2.10 ± 0.24 | 2.13 ± 0.26 | 0.94 ± 0.02 | 0.33 ± 0.23 | 0.10 ± 0.06 | 0.06 ± 0.04 |
| Spleen | 1.11 ± 0.12 | 0.65 ± 0.12 | 0.30 ± 0.04 | 0.11 ± 0.07 | 0.03 ± 0.04 | 0.03 ± 0.03 |
| Lung | 3.11 ± 0.22 | 2.44 ± 0.59 | 1.39 ± 0.12 | 0.64 ± 0.42 | 0.26 ± 0.06 | 0.10 ± 0.02 |
| Heart | 0.93 ± 0.06 | 0.64 ± 0.13 | 0.33 ± 0.04 | 0.19 ± 0.14 | 0.04 ± 0.02 | 0.00 ± 0.00 |
| Stomach | 1.12 ± 0.20 | 0.78 ± 0.22 | 0.88 ± 0.13 | 0.58 ± 0.40 | 0.74 ± 0.80 | 0.48 ± 0.19 |
| Brain | 0.21 ± 0.09 | 0.19 ± 0.18 | 0.06 ± 0.09 | 0.10 ± 0.13 | 0.01 ± 0.02 | 0.18 ± 0.23 |
| Blood | 2.29 ± 0.23 | 1.58 ± 0.25 | 0.67 ± 0.19 | 0.40 ± 0.12 | 0.16 ± 0.04 | 0.07 ± 0.01 |

Expressed in percentage of injection dose per gram of each tissue.
Each value shows mean ± S.D. in 3 to 5 animals.

(3) Binding Experiment using [$^{125}$I]I-BzA-TBOA Crude Membrane Preparation of Rat Brain Male Sprague-Dawley rats (body weight 200 to 250 g) were decapitated and the whole brain was taken out. The whole brain was quickly frozen in liquid nitrogen and stored at −80° C. until using. Under ice-cooling, the whole brain was homogenized in a Tris buffer (50 mM Tris-HCl (pH 7.4), 120 mM NaCl, 5 mM KCl, 2.5 mM CaCl$_2$, 1 mM MgCl$_2$) and centrifuged at 30,000×g at 4° C. for 20 minutes. The obtained pellet was re-suspended in the Tris buffer and the protein concentration was measured by using a protein assay kit (BioRad). The protein concentration was re-adjusted to 0.1 mg/100 μl and the obtained product was employed in the following binding experiments as a crude membrane preparation.

Competitive Binding Experiment

In the Tris buffer as described above, the concentration of 50 μl of [$^{125}$I]I-BzA-TBOA (200 Ci/mmol) was adjusted to 50 nM (final concentration 10 nM) while 100 μl of non-labeled TFB-TBOA was adjusted to $10^{-11}$ M, $10^{-10}$ M, $10^{-9}$ M, $10^{-8}$ M, $10^{-7}$ M, $10^{-6}$ M and $10^{-5}$ M, and DL-TBOA was adjusted to $10^{-10}$ M, $10^{-9}$ M, $10^{-8}$ M, $10^{-7}$ M, $10^{-6}$ M, $10^{-5}$ M and $10^{-4}$ M. 50 μl of [$^{125}$I]I-BzA-TBOA, 100 μl of the crude membrane preparation (0.1 mg/100 μl) and 100 μl of the Tris buffer containing or not containing non-labeled TFB-TBOA or DL-TBOA were mixed and incubated at 25° C. for 60 minutes. The reaction was ceased by adding 4 ml of ice-cooled Tris buffer. Then the reaction mixture was filtered through a GF/C filter (Whatman) having been soaked in a 0.1% poly-L-lysine hydrobromide solution at 4° C. overnight and washed three times with 4 ml portions of the Tris buffer. The radioactivity of the GF/C filter was measured with a γ-counter.

Data Analysis

The radioactivity of the sample incubated in the Tris buffer free from non-labeled TFB-TBOA was referred to as the total binding amount, while the radioactivity of the sample incubated in the Tris buffer containing $10^{-5}$ M of non-labeled TFB-TBOA was referred to as the nonspecific binding amount. Then the difference was calculated as the specific binding amount.

Figure 3:
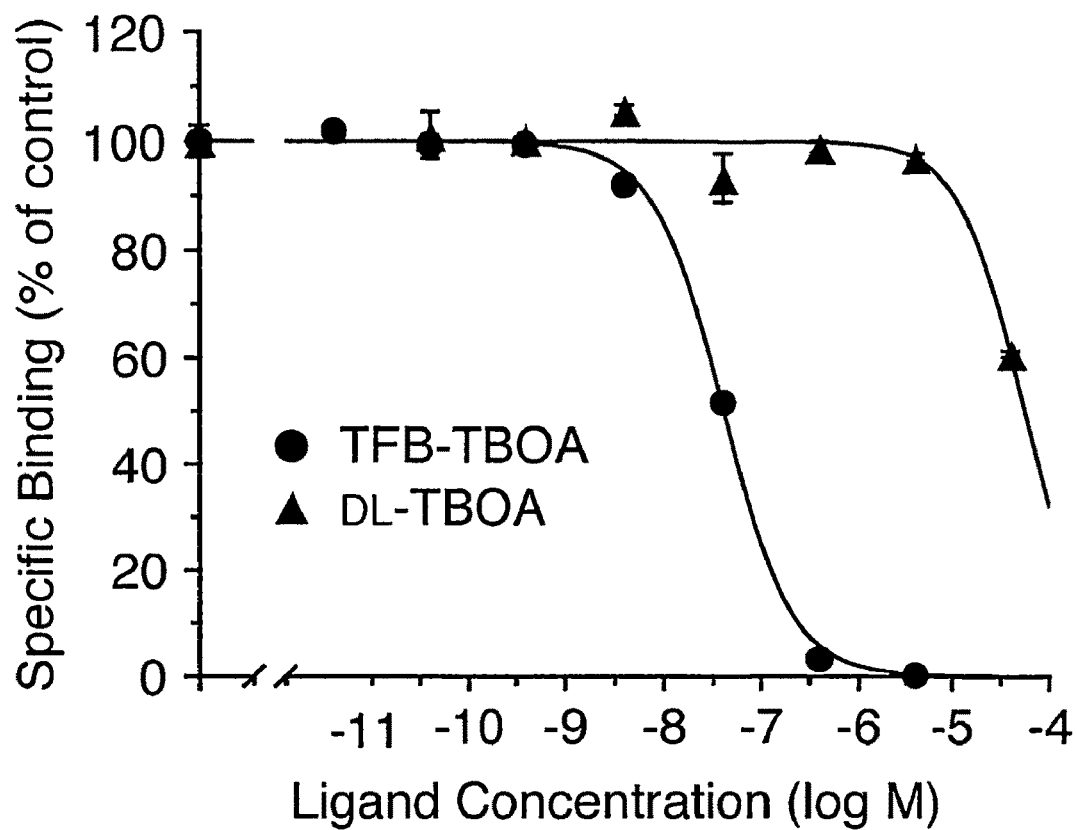
FIG. 3 shows substitution curves of glutamate transporter inhibitors in the specific binding system of 10 nM [$^{125}$I]I-BzA-TBOA to rat brain homogenate.

FIG. 3 shows the results.

(4) [$^{125}$I]I-BzA-TBOA Binding Experiment Using Brain Section Method

Male Sprague-Dawley rats (body weight 200 to 250 g) were decapitated and the whole brain was taken out. The whole brain was quickly frozen in dry ice powder and stored at −80° C. until using. Fresh frozen sections of 20 μm in thickness were prepared by using a cryostat, tightly layered onto a gelatin-coated slide glass plate and stored at −80° C. until using.

[$^{125}$I]I-BzA-TBOA (200 Ci/mmol) was diluted with a Tris buffer (50 mM Tris-HCl (pH 7.4), 120 mM NaCl, 5 mM KCl, 2.5 mM CaCl$_2$, 1 mM MgCl$_2$) to give a concentration of 1 nM and the brain sections prepared above were incubated at 25° C. for 60 minutes. In order to determine the nonspecific binding, 4 μM of TFB-TBOA was added. After the completion of the incubation, the brain sections were washed by being soaked in an ice-cooled Tris buffer for 5 minutes three times and in ice-cooled purified water for 5 minutes once, and then the brain sections were dried. Next, the sections were exposed to an imaging plate overnight and the radioactivity thus detected was analyzed by BAS2500.

Figure 4:
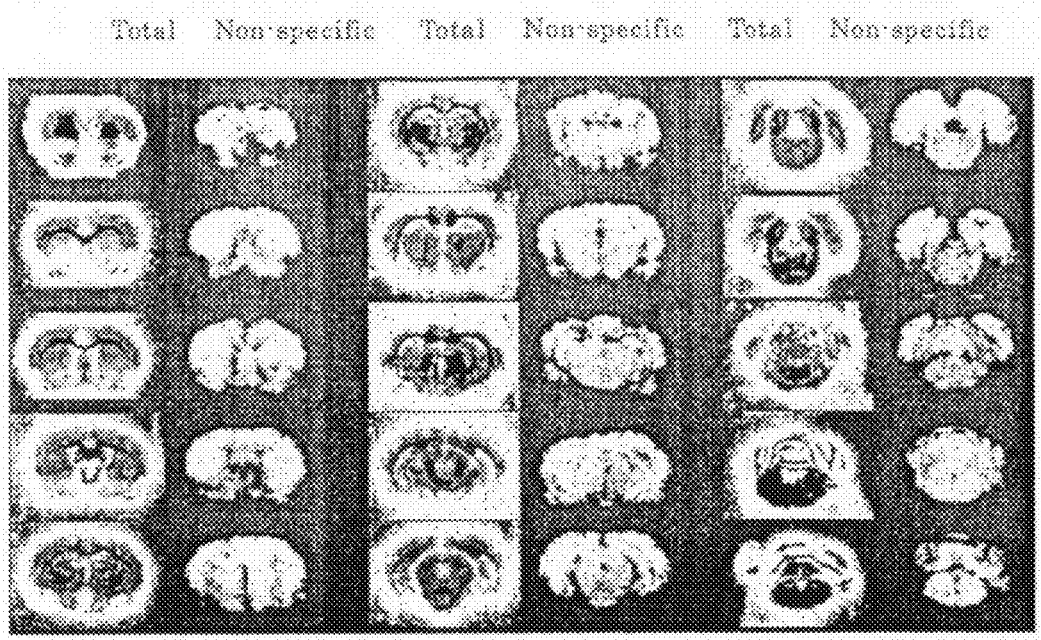
FIG. 4 shows the distribution of the binding sites of [$^{125}$I] I-BzA-TBOA in rat brain sections observed by use of 1 nM [$^{125}$I]I-BzA-TBOA.

FIG. 4 shows the results.

(5) Binding Experiment Using [$^3$H]Et-BzA-TBOA

Cell Membrane Preparation

About 20 ml of a medium contained in a T-flask (150 cm$^2$) was inoculated with COS-1 cells expressing EAAT which were then incubated therein until they reached confluence. After aspiration of the medium, the cells were washed with about 10 ml of phosphate buffered saline (PBS). After adding 4 ml of 0.25% trypsin/1 mM EDTA and allowing to stand for 5 minutes, 6 ml of the medium was added and the cells were collected into a 50 ml tube. Then they were centrifuged at 1200 rpm for 2 minutes and the supernatant was aspirated. The residue was thoroughly homogenized in a binding buffer (50 mM Tris-HCl (pH 7.4), 120 mM NaCl, 5 mM KCl, 2.5 mM CaCl$_2$, 1 mM MgCl$_2$) with the use of a Polytron homogenizer on ice. The homogenate was centrifuged at 30,000×g at 4° C. for 20 minutes. After discarding the supernatant, the pellet was re-suspended in an appropriate amount of the binding buffer to give a concentration of 100 to 500 μg/ml and homogenized again.

Binding Experiment

1) Binding Saturation Experiment

25 μl of [$^3$H]Et-BzA-TBOA at a concentration 10 times higher than the measurement concentration (50, 100, 250, 500 or 1000 nM), 25 μl of 100 μM of TFB-TBOA or the binding buffer were mixed with 200 µl of the above-described membrane preparation and the obtained mixture was incubated at room temperature for 60 minutes. Then the reaction was ceased by filtering the mixture through a GF/C filter (Whatman) having been soaked in a 0.1% poly-L-lysine hydrobromide solution for an hour followed by washing with 20 mM Tris buffer. After drying the filter, a solid scintillator MeltiLex A (PerkinElmer) was melted-on and the radioactivity was measured with a β-counter. The radioactivity of the sample free from TFB-TBOA was referred to as the total binding amount, while the radioactivity of the sample containing TFB-TBOA was referred to as the nonspecific binding amount. Then the difference was calculated as the specific binding amount.

FIG. 7 shows the saturation binding of ($^3$H)Et-BzA-TBOA to EAAT2, EAAT4, or EAAT5 expressed on COS-1 cells. FIG. 8 shows the results of Scatcherd analysis. $K_d$ values of respective subtypes were 26 nM (EAAT2), 13 nM (EAAT4) and 30 nM (EAAT5).

2) Competitive Substitution Experiment

Figure 9:
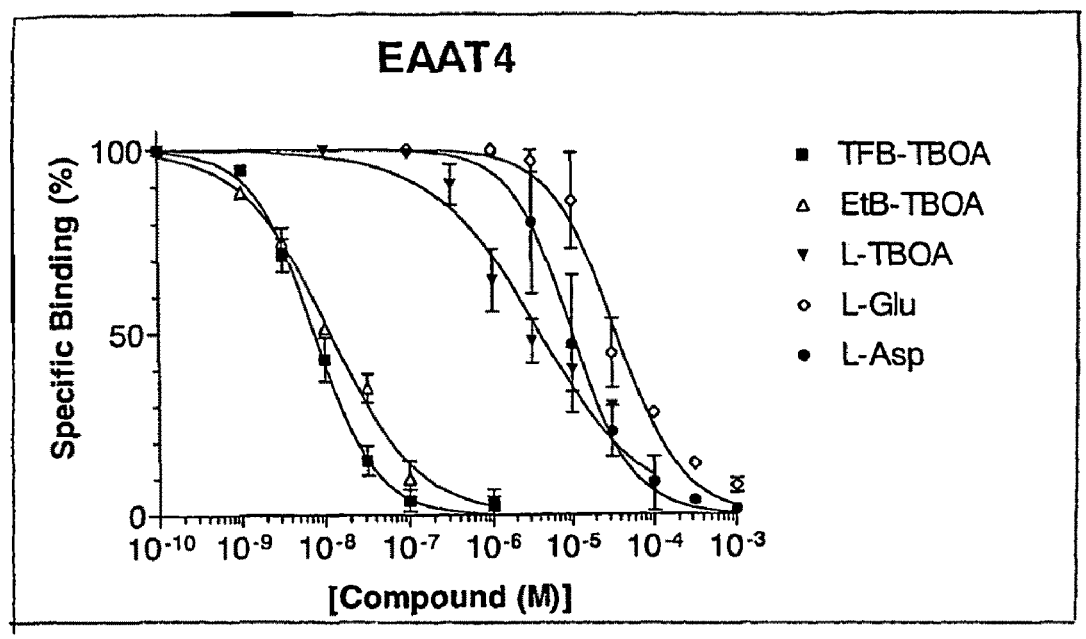
FIG. 9 shows substitution curves of glutamate transporter inhibitors in the specific binding system of [$^3$H]Et-BzA-TBOA to cell membrane homogenate.

25 µl of an inhibitor solution at a concentration 10 times higher than a predetermined concentration, 25 µl of 100 nM [$^3$H]Et-BzA-TBOA and 200 µl of the membrane preparation were mixed together and incubated at room temperature for 30 minutes. Then the reaction was ceased by filtering the mixture through a GF/C filter (Whatman) having been soaked in a 0.1% poly-L-lysine hydrobromide solution for an hour and followed by washing with 20 mM Tris buffer. After drying the filter, a MeltiLex A (Perkin Elmer) was melted-on and the radioactivity was measured with a β-counter. The radioactivity of the sample free from the inhibitor was referred to as the total binding amount, while the radioactivity of the sample containing 10 µM TFB-TBOA was referred to as the nonspecific binding amount. Then the difference was referred to as the specific binding amount and expressed in percentage of the total binding amount (FIG. 9).

The invention claimed is:

1. A 3-[3-(benzoylamido)benzyloxy]aspartic acid having a radioactive substituent on the benzoyl group which is represented by the following formula (1), or an ester or salt thereof:

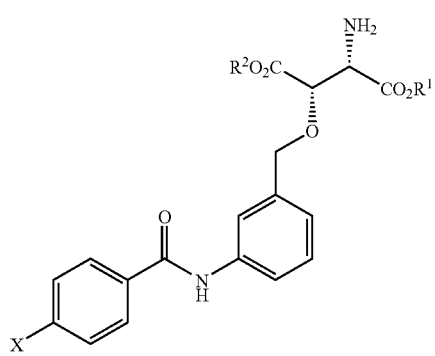

(1)

wherein X is $^{125}$I or a tritium-containing ethyl group (X=$C_2H_3T_2$); and $R^1$ and $R^2$ each represents a hydrogen atom, a straight or branched lower aliphatic alkyl group or an acetoxymethyl group.

2. A precursor compound of a compound as claimed in claim 1 represented by the following formula (2):

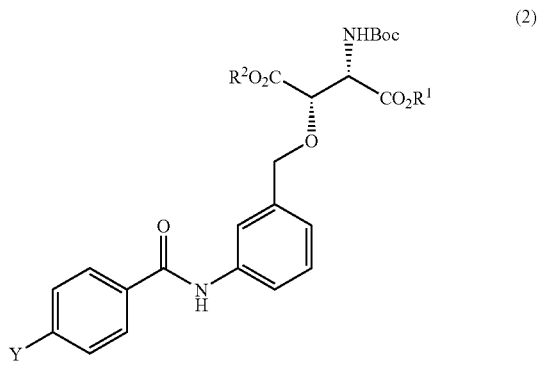

(2)

wherein $R^1$ and $R^2$ each represents a hydrogen atom, a straight or branched lower aliphatic alkyl group or an acetoxymethyl group; Y represents a leaving group to undergo a substitution reaction which is selected from an organometallic group, a halogen atom, a diazo group, a diazonium group, a trialkylammonium group and a nitro group; and Boc represents a t-butoxycarbonyl group.

3. The precursor compound as claimed in claim 2, wherein Y is —Sn(n-Bu)$_3$.

4. A method for producing a compound as claimed in claim 1 which comprises subjecting a precursor compound of formula (2)

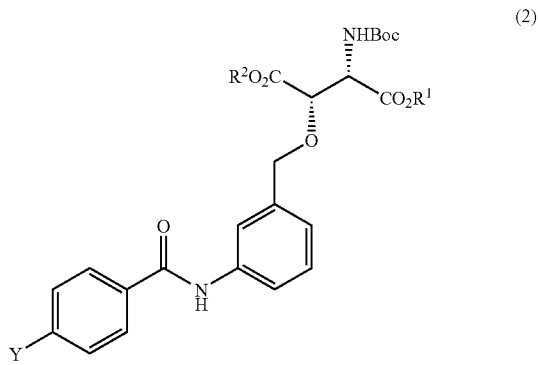

(2)

wherein $R^1$ and $R^2$ each represents a hydrogen atom, a straight or branched lower aliphatic alkyl group or an acetoxymethyl group; Y represents a leaving group to undergo a substitution reaction which is selected from an organometallic group, a halogen atom, a diazo group, a diazonium group, a trialkylammonium group and a nitro group; and Boc represents a t-butoxycarbonyl group, to an exchange reaction with a radioactive atom and then removing the protecting group to give a compound of the formula (2).

5. The method as claimed in claim 4 which comprises subjecting the precursor compound of formula (2) wherein Y is —Sn(n-Bu)$_3$ to an oxidative tin-iodine exchange reaction with Na$^{125}$I in the presence of an oxidizing agent and acetic acid to thereby give a compound of formula (1) wherein X is $^{125}$I.

6. A radiolabeled inhibitor of glutamate transporter activity comprising a compound as claimed in claim 1.

7. A radioactive ligand to a glutamate transporter comprising a compound as claimed in claim 1.

8. A method for examining distribution and/or expression of glutamate transporter and/or glutamate uptake level in a biological sample which comprises:

a) contacting the biological sample with a compound as claimed in claim 1, an inhibitor as claimed in claim 6 or a ligand as claimed in claim 7;

b) detecting the presence or absence of the compound, the inhibitor or the ligand having bound specifically to the biological sample with the use of the radioactivity as an indicator; and c) in the case where the specific binding is observed in the above step b), estimating that the glutamate transporter is distributed or expressed in the biological sample or that the part of the body from which the biological sample was obtained participates in glutamate uptake.

9. A compound as claimed in claim 1 wherein, in the formula (1), X is a tritium-containing ethyl group (X=$C_2H_3T_2$), and each of $R^1$ and $R^2$ is a hydrogen atom.

10. A precursor compound of a compound of the formula (1) as claimed in claim 9 which is represented by the following formula (3):

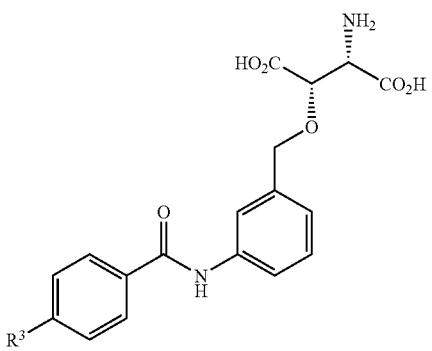

wherein $R^3$ is a vinyl group.

11. A method for producing a compound of the formula (1) as claimed in claim 9 which comprises reacting a precursor compound of the formula (3) with tritium gas in the presence of a palladium catalyst.

\* \* \* \* \*